(12) United States Patent
Bunquin et al.

(10) Patent No.: US 8,901,334 B2
(45) Date of Patent: Dec. 2, 2014

(54) TRANSITION METAL-PHOSPHORANIMIDE CATALYSTS

(71) Applicant: Governors of the University of Alberta, Alberta (CA)

(72) Inventors: Jeffrey Camacho Bunquin, Alberta (CA); Jeffrey Mark Stryker, Alberta (CA)

(73) Assignee: Governors of the University of Alberta (CA)

( * ) Notice: Subject to any disclaimer, the term of this patent is extended or adjusted under 35 U.S.C. 154(b) by 122 days.

(21) Appl. No.: 13/725,676

(22) Filed: Dec. 21, 2012

(65) Prior Publication Data

US 2014/0179943 A1 Jun. 26, 2014

(51) Int. Cl.
| | | |
|---|---|---|
| *C07F 15/00* | (2006.01) | |
| *B01J 31/22* | (2006.01) | |
| *C07F 15/02* | (2006.01) | |
| *C07F 15/04* | (2006.01) | |
| *C07F 15/06* | (2006.01) | |
| *B01J 31/18* | (2006.01) | |

(52) U.S. Cl.
CPC ............ *B01J 31/22* (2013.01); *C07F 15/025* (2013.01); *C07F 15/045* (2013.01); *C07F 15/065* (2013.01); *B01J 31/189* (2013.01)
USPC .......................................... 556/21; 502/162

(58) Field of Classification Search
CPC .... C07F 15/025; C07F 15/045; C07F 15/065; B01J 31/189
USPC .......................................... 556/21; 502/162
See application file for complete search history.

(56) References Cited

U.S. PATENT DOCUMENTS

| | | | |
|---|---|---|---|
| 6,239,061 B1 | 5/2001 | Wang et al. | |
| 6,300,435 B1 * | 10/2001 | Gao et al. ..................... | 526/133 |
| 6,846,769 B2 | 1/2005 | Arndt-Rosenau et al. | |

FOREIGN PATENT DOCUMENTS

| | | |
|---|---|---|
| CA | 2605077 | 4/2009 |
| EP | 0881233 | 12/1998 |
| EP | 0890581 | 1/1999 |
| WO | WO 00/05236 | 2/2000 |
| WO | WO 00/05238 | 2/2000 |
| WO | WO 01/19512 | 3/2001 |
| WO | WO 2009/043156 | 4/2009 |
| WO | WO 2009/043157 | 4/2009 |

OTHER PUBLICATIONS

Dehnicke et al., "Phosphoraneiminato complexes of transition metals," Coordination Chemistry Reviews, 1999, vol. 182, Iss. 1, pp. 19-65.

Guerin et al., "Synthesis, Structure, and Reactivity of the Phosphinimide Complexes $(tBu_3PN)_nMX_{4-n}(M = Ti, Zr)$," Organometallics, 2000, vol. 19, Iss. 16, pp. 2994-3000.

(Continued)

*Primary Examiner* — Porfirio Nazario Gonzalez
(74) *Attorney, Agent, or Firm* — Sheridan Ross, P.C.

(57) ABSTRACT

Phosphoranimide-metal catalysts are disclosed. The catalysts comprise first row transition metals such as nickel, cobalt or iron. The hydrocarbon-soluble catalysts have a metal to anionic phosphoranimide ratio of 1:1, have no inactive bulk phase and no dative ancillary ligands, and are active for a range of commercially important reductive transformations. A method of synthesis of these catalysts by reduction of a precursor of these catalysts is also disclosed.

23 Claims, 3 Drawing Sheets

Structure of $[Ni(NP^tBu_3)]_4$.

(56) References Cited

OTHER PUBLICATIONS

Klien et al., "Novel Imido- and Phosphorane-Imido-Nickel(II) Complexes. Crystal and Molecular Structure of ($\mu_3$-NH)($\mu_3$-NPMe$_3$)(NiClPMe$_3$)$_3$," Journal of the American Chemical Society, 1991, vol. 113, pp. 4673-4675.

Mast et al., "Vinyl-type polymerization of norbornene by a nickel-based catalyst with phosphoraneiminato ligands," Macromolecular Rapid Communications, 1999, vol. 20, Iss. 4, pp. 232-235.

Ramos et al., "Titanium ferrocenyl-phosphinimide complexes," Dalton Transactions, 2010, vol. 39, Iss. 5, pp. 1328-1338.

Riese et al., Cobalt(II)—organische Phosphaniminato-Komplexe mit Heterocuban-Struktur. Kristallstrukturen von [CoBr(NPR$_3$)]$_4$ mit R = Me, Et,[Co(C≡C-CMe$_3$)(NPMe$_3$)]$_4$ und [Co(C≡C-SiMe$_3$)(NPEt$_3$)]$_4$, Zeitschrift für anorganische und allgemeine Chemie (Journal of Inorganic and General Chemistry), 1998, vol. 624, Iss. 8, pp. 1279-1284.

Schroers et al., "Grafting of Vinyl-Type Polynorbornene on Polybutadiene and Polyisoprene," Macromolecular Chemistry and Physics, 2002, vol. 203, Iss. 18, pp. 2658-2664.

Yadav et al., "Phosphinimide complexes with pendant hemilabile donors: synthesis, structure and ethylene polymerization activity," Dalton Transactions, 2009, Iss. 9, pp. 1636-1643.

\* cited by examiner

Structure of [Ni(NP$^t$Bu$_3$)]$_4$.

Structure of [Co(NP$^t$Bu$_3$)]$_4$ where M = Co.

Structure of $[Cl_2Co_2(\mu-NP^tBu_3)_2(THF)_2]$.

TRANSITION METAL-PHOSPHORANIMIDE CATALYSTS

FIELD

This disclosure relates to first row transition metal catalysts and the synthesis of these catalysts. More particularly, the phosphoranimide-transition metal catalysts can catalyze a range of organic transformations including hydrodesulfurization and hydrogenation.

BACKGROUND

Catalytic reduction of organic substrates remains a key enabling industrial process that sustains several major chemical industries. There is a wide range of commercially-important reductive transformations catalyzed by transition metals catalysts. For example, the transition-metal catalyzed cleavage of polar bonds such as C—S and C—N bonds, and hydrogenation of unsaturated functional groups such as alkenes (to alkanes) are reductive transformations pertinent to fine chemicals synthesis and to the production of environmentally safe fuel from crude petroleum feedstock.

Current industrial processes employing catalytic reduction are commonly mediated by relatively expensive, rare and in some cases, toxic second- and third-row transition metals. The use of these rare transition metals raises barriers to the sustainability of these industrial processes. As an example, current technologies for the upgrading of petroleum feedstocks which include hydrodesulfurization (HDS) and hydrodenitrogenation (HDN) are energy intensive. This is due in part to the reaction conditions required for the metal catalysts currently used for these processes. Molybdenum and tungsten catalysts, promoted by cobalt and nickel ions such as $CoMoS_2$ and $NiWS_2$, generally function under high temperature (e.g. about 300 to 650° C.) and high pressure (e.g. about 90 to 120 atm). These conditions contribute to refining costs of petroleum and crude oil, hence, there is a demand for cost-effective and environmentally benign catalytic processes for industrial scale production of commodity chemicals and fuels.

First row transition metals are relatively inexpensive and abundant. This makes them attractive candidates [inter alia] for catalytic hydrogenation and the processing of petroleum feedstocks. Generally, however, first-row transition metal catalysts are believed to possess intrinsically low activity.

Discrete ligand-supported metal clusters have been used to model the active sites of heterogeneous catalysts and, in some cases, catalyze organic reactions. Polymetallic catalysts typically display reactivity different from monomeric catalysts. Ligand-supported metal clusters can be classified according to the relative saturation of the metal centers: coordinatively saturated clusters are relatively stable and inert, normally requiring activation prior to use. Generally, coordinatively unsaturated clusters are thermodynamically less stabilized and more reactive. Therefore, coordinatively unsaturated clusters are good candidates for catalysis.

SUMMARY OF THE INVENTION

According to one aspect, there is provided a transition metal catalyst comprising monomeric units of the general Formula I:

[MNPR$_3$]  Formula I where M is a first row transition metal having a +1 oxidation state;

$R_3PN^-$ is a monoanioinic phosphoranimide ligand of structure:

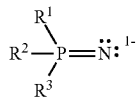

where:
R$^1$, R$^2$, R$^3$ can be the same group or different groups; R$^1$, R$^2$, R$^3$=alkyl (C1-18, primary, secondary and tertiary alkyl), cycloalkyl (C3-C8), aryl/heteroaryl, substituted aryl/heteroaryl or an inert functional group containing at least one heteroatom selected from the group consisting of a Group 15 and/or Group 16 element; R$^1$, R$^2$, R$^3$ may also be linked to give cyclic systems, using linkages such as aliphatic cyclic systems; wherein the M to R3PN$^-$ ratio in the catalyst is 1:1.

According to a second aspect, there is provided a method of synthesis of a transition metal catalyst comprising reducing a complex of Formula II [MNPR$_3$X$_{(m-1)}$]$_n$ with a reducing agent to produce a catalyst of Formula I [MNPR$_3$], wherein Formula II is

[MNPR$_3$X$_{(m-1)}$]$_n$ where:
m=2 to 3; n=1 to 4; M is Fe, Co or Ni; X$^-$ can be any halide or pseudohalide;

$R_3PN^-$ is a monoanionic phosphoranimide ligand of structure:

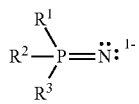

where
R$^1$, R$^2$, R$^3$ are the same group or different groups; R$^1$, R$^2$, R$^3$=alkyl (C1-18, primary, secondary and tertiary alkyl), cycloalkyl (C3-C8), aryl/heteroaryl, substituted aryl/heteroaryl or an inert functional group optionally containing at least one heteroatom, and wherein the substituents may also be linked to give cyclic systems, both aliphatic and aromatic; the M:NPR3 ratio is 1:1; and wherein in Formula I, M and NPR$_3$ are as defined for the compound of Formula II and wherein the M:NPR3 ratio is 1:1.

According to a third aspect, there is provided a method of synthesis of [FeNP$^t$Bu$_3$]$_4$ comprising: reacting a compound of formula [Br$_2$Fe$_2$(μ-NP$^t$Bu$_3$)$_2$] with Na(Hg) at −35° C.

According to a fourth aspect, there is provided a method of synthesis of [CoNP$^t$Bu$_3$]$_4$ comprising: reacting a compound of formula [Cl$_2$Co$_2$(μ-NP$^t$Bu$_3$)$_2$(THF)$_2$] with Na(Hg) at −35° C.

According to a fifth aspect, there is provided a method of synthesis of [NiNP$^t$Bu$_3$]$_4$ comprising: reacting a compound of formula [Br$_2$Ni$_2$(μ-NP$^t$Bu$_3$)$_2$] with Na(Hg) at −35° C.

According to a sixth aspect, there is provided a method of synthesis of complex of Formula II from an anionic metathesis reaction between a metal salt selected from the group consisting of MX$_m$ and L$_a$MX$_m$ and an alkali or alkaline metal salt of a phosphoranimide ligand, wherein Formula II is defined as follows:

[MNPR$_3$X$_{(m-1)}$]$_n$ where:

m=2 to 3; n=1 to 4; M is Fe, Co or Ni. X⁻ can be any halide or pseudohalide;

$R_3PN^-$ is a monoanioinic phosphoranimide ligand of structure:

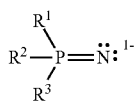

Where:

$R^1$, $R^2$, $R^3$ can be the same group or different groups; $R^1$, $R^2$, $R^3$=alkyl (C1-18, primary, secondary and tertiary alkyl), cycloalkyl (C3-C8), aryl/heteroaryl, substituted aryl/heteroaryl or an inert functional group optionally containing at least one heteroatom, and wherein the substituents may also be linked to give cyclic systems, both aliphatic and aromatic; the ratio of $NPR_3$ to M is 1:1; and wherein in $MX_m$ and $L_aMX_m$:

m=2 to 3; a=1 to 4; M can be any first row transition metals; X⁻ can be any halide or pseudohalide; L can be a two-electron dative donor molecule selected from the group of dialkyl ethers consisting of tetrahydrofuran, 1,2-dimethoxyethane, dioxane; or selected from the group consisting of trialkylphosphine or a triarylphosphine selected from the group consisting of triphenylphosphine and tri-(p-tolyl)phosphine.

DETAILED DESCRIPTION

Figure 1:
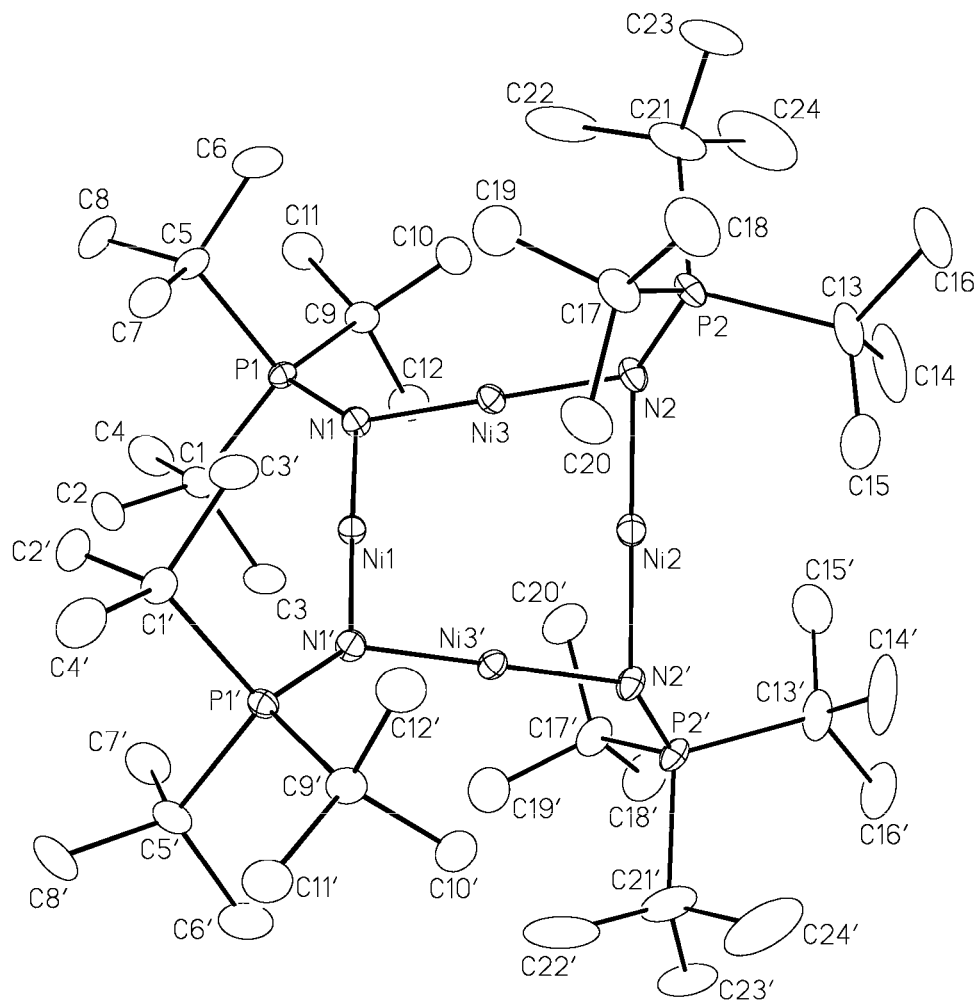
FIG. 1 shows an ORTEP diagram depicting the X-ray crystal structure of $[Ni(NP^tBu_3)]_4$.

Molecular transition metal clusters have been used as models for heterogeneous catalyst active sites. However, the synthesis of coordinatively unsaturated molecular transition metal clusters is difficult because of the instability of these clusters. Known clusters have a metal core (comprising two or more metal centers) supported by large, often polyfunctional ligands. Accordingly, the metal centers are generally sterically hindered by the bulky surrounding ligands and the metal cluster is typically coordinatively saturated. This property of coordinative saturation limits the utility of these clusters for catalysis because the metal in the cluster must become coordinatively unsaturated in order to bind substrate and engage in catalytic activity.

The rational design of coordinately unsaturated metal clusters benefits from studies of monometallic two-coordinate transition metal complexes. These complexes are the most coordinatively unsaturated metal complexes that have been prepared. Two-coordinate transition metal complexes have special electronic and magnetic properties. Of the 80 structurally characterized two-coordinate transition metal complexes, all are monomeric and stabilized by bulky anionic ligands. These two-coordinate metal complexes can act as precursors for the synthesis of transition metal nanoparticles. In addition, these complexes can be used for the preparation of supported heterogeneous catalysts.

Many industrial catalysts are transition metal catalysts. Second and third row transition metals are most frequently associated with high reactivity, but these are scarce and expensive, which adds to processing costs. Also, some transition metal catalysts may be toxic. As a result, first row transition metals, which are cheaper, abundant, and often less toxic, may become useful candidates for catalysis, provided an appropriate coordination environment is identified.

DEFINITIONS

As used throughout the disclosure, the term "alkyl" includes $C_1$ to $C_{18}$ straight chain, branched or cyclic alkyl groups such as, but not limited to, ethyl, propyl, isopropyl and t-butyl.

The term "aryl" includes aromatic hydrocarbons as substituents. Aryl groups may have one or more aromatic rings, which may be fused or connected by a connecting group or a bond. Aryl groups may also include one or more alkyl or aryl substituents located on the aryl group. Specific though non-limiting examples include, phenyl, tolyl, naphthenyl and biphenyl.

The term "heteroaryl" includes aromatic hydrocarbons which contain at least one heteroatom in the ring. Similar to the aryl groups, heteroaryls may have one or more aromatic rings which may be fused or connected by a connecting group or a bond.

The term "inert functional group" designates heteroatom-bearing hydrocarbyl fragments attached via the heteroatom to aryl and heteroaryl ligand substituents, as defined above, or appended to the terminus of a ligand substituent. The former serve to modulate, electronically and/or sterically, the chemical nature of the phosphoranimide ligand(s), changing but not impeding catalyst performance. The latter can function as a point of further chemical attachment(s) (i.e., derivatization), for example, in order to construct supported heterogeneous catalysts comprising chemically bonded or linked phosphoranimidometal catalyst subunits grafted onto conventional catalyst supports.

The term "heteroatom" refers to a Group 14, 15 or 16 element, preferably Si, N or O.

The term "pseudohalide" refers to anions with similar properties to halides preferably $OSO_2R^-$, where R=Me, Ph, p-Tol, $CF_3$.

Catalysts

The present disclosure provides a class of transition metal catalysts comprising an assembly of monomeric units having the general Formula I:

[M(NPR₃)]                                                    Formula I wherein

M is a first row transition metal having a +1 oxidation state;
the ratio of M to $R_3PN^-$ is 1:1;
$R_3PN^-$ is a monoanioinic phosphoranimide ligand which supports the metal centers;
$R_3PN^-$ has the following structure:

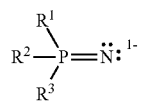

where:

$R^1$, $R^2$, $R^3$ can be the same group or different groups;
$R^1$, $R^2$, $R^3$=alkyl (C1-18, primary, secondary or tertiary alkyl), cycloalkyl (C3-C8), aryl/heteroaryl, substituted aryl/heteroaryl or an inert functional group containing at least one heteroatom; and $R^1$, $R^2$, $R^3$ may also be linked to give cyclic systems, using linkages such as aliphatic cyclic systems [(e.g., R1/R2=—$(CH_2)_n$—, where n=3-10].

In one embodiment, the transition metal may be Mn, Fe, Co, or Ni. In the Examples, Fe, Co and Ni are suitable metal centers for the catalysts.

The catalysts will be referred to throughout this disclosure as catalysts or complexes of general Formula II:

$$[M(NPR_3)]_n \qquad \text{Formula II}$$

where:
n=is a whole number;
M and $NPR_3$ is as defined above for the compound of Formula I; and
the ratio of M to $NPR_3$ is 1:1.

The value for n can vary with the monoanionic phosphoranimide ligand R3PN⁻. For example, the catalysts may have n values of greater than 2. In one embodiment, n is 2 to 8.

The chemical composition of any catalyst described in this disclosure is consistent with a substance where the M to $R_3PN^-$ ratio is 1:1.

In one embodiment, the structurally characterized catalysts with formula $[MNPR_3]n$ are discrete tetrametallic transition metal clusters having the following general formula:

$$[M(NPR_3)]_4 \qquad \text{Formula III}$$

wherein M and $NPR_3$ are as defined above in the compound of Formula I.

As is evident from general Formula II, the catalysts are free from ancillary ligands which could inhibit the catalytic activity of the metal centers. For example, bulky ancillary ligands could render the metal centers less accessible, and thus limiting reactivity and scope. In the catalysts of Formula II, the bridging phosphoranimide ligands achieve essentially the same effect as the bulky ligands (i.e. the metal centers are stabilized, low coordinate metal centers), but without the steric hindrance effects. Also, the variability in the possible ligands in the presently disclosed catalysts allows for a range of different properties of the catalysts, but all having the common features of being catalytically active and being hydrocarbon-soluble.

As a specific example, the catalysts of Formula III are discrete tetrametallic transition metal clusters having the following structural formula, designated herein as Formula II:

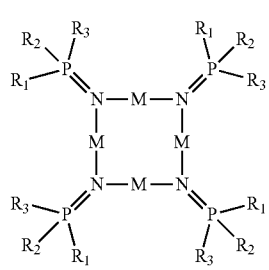

Formula III where
the ratio of M to $NPR_3$ is 1:1; and
M and $NPR_3$ are as defined in the compound of Formula I.

The complexes of Formula III have metal centers which are supported by bridging, anionic phosphoranimide ligands. Each tetrametallic cluster consists of four monophosphoranimidometal (I) [$MNPR_3$] complexes as monomeric units.

Monophosphoranimidometal (I) monomers are the building blocks of the catalysts of the present disclosure. Compared to the corresponding neutral trialkylphosphine ligands, the phosphoranimide (P=N) functional group displaces the R groups further away from the metal centers, allowing for steric accessibility of the metal centers. This, in conjunction with the absence of ancillary ligands or exogenous donor molecules, allows for the formation of coordinatively unsaturated metal centers in the catalysts. The phosphoranimide nitrogen center provides two donor electron pairs, which leads to bridging coordination at the nitrogen and short metal-metal distances. This nucleates metal clusters consisting of nitrogen-linked phosphoranimidometal (I) monomer units.

As a person skilled in the art would appreciate, complexes of Formula II can adapt various modes of aggregation. As a result, compounds of Formula II represent a library of catalysts. Structurally characterized compounds of Formula III comprise a subclass of catalysts of Formula II. Compounds of Formula III result from the aggregation of four monomeric units of Formula I. Catalysts supported with phosphoranimide ligands of similar electronic and steric properties with, for example, tri-t-butylphosphoranimide may adopt such tetrameric structure. However, unless specifically provided in the Examples, the catalysts of the present disclosure do not represent a particular characterized structure.

In relation to structurally characterized catalysts of Formula III, the metal phosphoranimide catalysts that Dehnicke reported have different cluster dimensionality (e.g. a heterocubane) and metal oxidation state (see, for example, Dehnicke et al., (1998), *Phosphoraneiminato Complexes of Transition Metals*, Coordination Chemistry Reviews, 182 (1999) 19-65). The catalysts of Formula III have a planar or pseudoplanar tetrametallic core with each metal center at the +1 oxidation state.

Furthermore, the low oxidation state of the metal centers in these catalysts make them amenable to oxidative passivation. For example, the catalysts can be treated by a sulfur reagent, such as $S_8$, to prepare air-stable sulfided catalyst derivatives. Transition metal sulfides are industrially useful precatalysts for hydrogenation and hydrodesulfurization of petroleum feedstocks.

The present disclosure also relates to a method of synthesis of these catalysts. The method of synthesis involves a first step of anionic ligand methathesis with a metal halide precursor resulting in the formation of a halide-functionalized metal phosphoranimide complex, followed by chemical reduction of this complex. The two steps can be conducted sequentially, without isolation of the intermediate halide complex. In some cases, the intermediate halide complex is isolated prior to reduction. This method of synthesis is carried out under an inert atmosphere. The halide-functionalized metal phosphoranimide complex has the general Formula IV:

$$[MNPR_3X_m]_n \qquad \text{Formula IV}$$

where:
m=1 or 2;
n=2 to 4;
M to $R_3PN^-$ ratio is 1:1;
M is a first row transition metal;
$X^-$ can be any halide or pseudohalide;
$R^1$, $R^2$, $R^3$ can be the same group or different groups;
$R^1$, $R^2$, $R^3$=alkyl (C1-18, primary, secondary and tertiary alkyl), cycloalkyl (C3-C8), aryl/heteroaryl, substituted aryl/heteroaryl or an inert functional group optionally containing at least one heteroatom; and
the substituents may also be linked by aliphatic hydrocarbyl groups to give cyclic systems [(e.g., R1/R2=—$(CH_2)_n$—, where n=3-10].

In some embodiments, the transition metal may be, but is limited to, Mn, Fe, Co or Ni. In the Examples, Fe, Co and Ni are suitable as the metal centers. In addition, in some embodiments, $X^-$ can be, but is not limited to, $F^-$, $Cl^-$, $Br^-$, $I^-$, or $OSO_2R^-$, where R=Me, Ph, p-Tol, $CF_3$.

In one aspect, there is provided a process for the synthesis of a complex of Formula II via treatment of a complex with Formula V with a reducing agent. The complex of Formula V has the following structure:

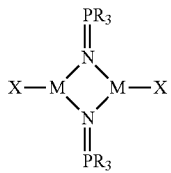

Formula V where:
M to $R_3PN^-$ ratio is 1:1;
M is a first row transition metal;
$X^-$ can be any halide or pseudohalide:
$R^1$, $R^2$, $R^3$ can be the same group or different groups;
$R^1$, $R^2$, $R^3$=alkyl (C1-18, primary, secondary and tertiary alkyl), cycloalkyl (C3-C8), aryl/heteroaryl, substituted aryl/heteroaryl or an inert functional group optionally containing at least one heteroatom; and
the substituents may also be linked to give cyclic systems, both aliphatic and aromatic [(e.g., R1/R2=—$(CH_2)_n$—, where n=3-10]

In some embodiments, the transition metal may be, but is limited to, Mn, Fe, Co or Ni. In the Examples, Fe, Co and Ni are suitable as the metal centers. In addition, in some embodiments, $X^-$ can be, but is not limited to, $F^-$, $Cl^-$, $Br^-$, $I^-$, or $OSO_2R^-$, where R=Me, Ph, p-Tol, $CF_3$.

The reducing agent may be comprised of a metal such as, but not limited to, Li, Na, or K. It should also be apparent to a person skilled in the art that metal reducing agents may exist in various forms such as, but not limited to, sodium naphthalenide, Na(Hg) amalgam, Na—K alloy, or $KC_8$.

The reduction step can be carried out in inert organic solvents such as tetrahydrofuran, hexane, benzene, diethyl ether or toluene, for example. However, halogen-containing solvents are generally unsuccessful in this reduction step.

The ratio of the reducing agent to complex of Formula IV can range from about 1:1 to about 2:1. Ratios in excess of this can be also used for the reduction, but are not necessary.

The reduction step can be conducted at low to ambient temperatures. For example, temperatures may range from about −80 to 25° C. may be used. The preferred reaction temperature varies with the choice of reducing agent. As an example, the reduction step for the synthesis of [Co(NP$^t$Bu$_3$)]$_4$ as detailed herein is suitably carried out at −35° C.

In another embodiment, there is disclosed a method for the synthesis of the complex of Formula III from an anionic metathesis reaction between a metal halide ($MX_m$) and an alkali or alkaline metal salt of a phosphoranimide ligand. The metal precursor can be a metal salt such as $MX_m$ or a solvated metal salt such as $L_aMX_m$. This reaction is as illustrated below:

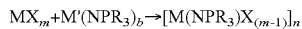

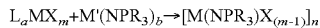

where:
M'(NPR$_3$)$_b$ is a Group I or Group II metal phosphoranimide salt and wherein the anionic phosphoranimide $R_3PN^-$ ligand is as defined above for Formula I;
m=2 to 3;
n=1 to 4;
a=1 to 3;
b=1 or 3;
M to $R_3PN^-$ ratio in the complex of formula $[M(NPR_3)X_{(m-1)}]_n$ is 1:1;
M is a first row transition metal;
$X^-$ is a halide or pseudohalide:
L can be a two-electron dative donor molecule selected from the group of dialkyl ethers such as, but not limited to, tetrahydrofuran, 1,2-dimethoxyethane, dioxane; or selected from the group of trialkylphosphine or a triarylphosphine such as, but not limited to triphenylphosphine or tri-(p-tolyl)phosphine; and
M' can be an alkali or alkaline metal. Alkali phosphoranimide salts (i.e. M'(NPR$_3$)$_b$) employed in the synthesis can include monophosphoranimide salts of lithium, sodium, potassium, and cesium; and alkaline earth metal phosphoranimide salts can include [Mg(NPR$_3$)$_2$].

Furthermore, the synthesis of complexes of general formula $[M(NPR_3)X_{(m-1)}]_n$ can also be carried out from the treatment of a metal salt $MX_m$ or $L_aMX_m$ with a magnesium phosphoranimide reagent of general formula [Mg(NPR$_3$)X] wherein $MX_m$, $L_aMX_m$, $R_3PN^-$ and X— are as defined above.

In some embodiments, the transition metal may be, but is limited to, Mn, Fe, Co or Ni. In addition, in some embodiments, $X^-$ can be, but is not limited to, F, $Cl^-$, $Br^-$, $I^-$, or $OSO_2R^-$, where R=Me, Ph, p-Tol, $CF_3$.

In general, the efficient synthesis of complexes of general formula $[M(NPR_3)X_{(m-1)}]_n$ may be carried out at a M to $R_3PN^-$ ratio of about 1:1 or greater. The suitable ratio of the metal salt to M'(NPR$_3$)$_b$ varies with the specific metal, leaving group (X) and M'(NPR$_3$)$_b$ reagent. When b=1 or when a [Mg(NPR$_3$)X] reagent is used, the ratio of the metal salt to M'(NPR$_3$)$_b$ a ratio of about 1:1 can be employed for the synthesis; however, yields are generally higher in the presence of an excess of the metal salt, for example, 2:1. When b=2, the ratio may be range from 2:1 to 4:1 to ensure that the M to R3PN$^-$ ratio of about 1:1 or greater is maintained.

The anionic metathesis can be conducted in low to ambient temperatures. For example, temperatures may range from about −80 to 25° C. The anionic metathesis reaction is preferably conducted at temperature ranging from −75 to −35° C., as demonstrated in the synthesis of [Co(NP$^t$Bu$_3$)]$_4$ and [Ni(NP$^t$Bu$_3$)]$_4$ described herein.

The synthetic strategy employed provides a method for the synthesis of other tetrameric monoimidometal (I), {LM}$_n$, catalysts wherein the M to L ratio is maintained at 1:1. These catalysts can be supported by bridging, monoanionic imido-type ligands such as, but not limited to, trialkylphosphoranimides.

The non-limiting examples below serve to illustrate the embodiments described above.

EXAMPLES

Example 1

[Ni(NP$^t$Bu$_3$)]$_4$ and Method of Synthesis

A nickel phosphoranimide catalyst (shown in FIG. 1 and referred to herein as the Ni(I) catalyst) having the formula shown below is synthesized as an example:

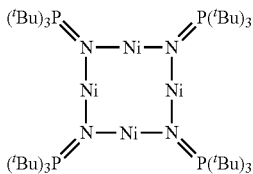

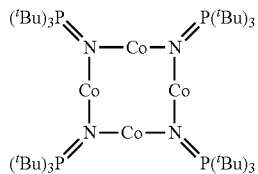

To prepare this catalyst, 1.62 mmol of (dme)NiBr$_2$ and 0.81 mmol LiNP$^t$Bu$_3$ are separately suspended in 5 mL portions of tetrahydrofuran (THF) in 15 mL screw-capped vials under an inert atmosphere, for example, in a nitrogen- or argon-filled drybox. Both suspensions are cooled to −35° C. in a dry-box freezer for an hour. The LiNP$^t$Bu$_3$ suspension is added dropwise into the metal halide suspension with occasional stirring over a four-hour period with the temperature constant at −35° C. After the addition of the ligand, the reaction mixture is left in the freezer overnight. The solvent is removed in vacuo and the residue is washed with 4 mL portions of hexane thrice. The residue is dissolved in 7 mL THF, charged with 2.5 mmol of Na delivered using a 1% Na/Hg reagent and stirred overnight. The solvent is evaporated and the product is extracted with pentane and filtered through a plug of Celite. The solvent is removed. This reaction gave an 80% yield. The product precipitates as dark green prismatic crystals from a concentrated THF solution upon cooling to −35° C. The product is characterized by X-ray crystallography, magnetic susceptibility measurement by the Evan's method (Evans, D. F. J. J. Chem. Soc. 1959, 2003-2005, which is herein incorporated by reference) and elemental analysis (vide infra).

FIG. 1 shows an ORTEP (Oak Ridge Thermal Ellipsoid Plot Program) diagram depicting the X-ray crystal structure of [Ni(NP$^t$Bu$_3$)]$_4$. The calculated elemental composition of the Ni(I) catalyst is C, 52.41%; H, 9.90%; N, 5.09%. The determined elemental composition is C, 52.38%; H, 9.89%; N, 4.96%. Solution magnetic susceptibility experiments revealed that the Ni(I) catalyst is a 3.50-electron paramagnet ($\mu_{eff}$=4.40$\mu_{Bo}$) at room temperature.

Example 2

[Ni(NP$^t$Cy$_3$)]$_n$ and Method of Synthesis

A nickel phosphoranimide catalyst of the formula [Ni(NP$^t$Cy$_3$)]$_n$ is synthesized as an example.

To prepare this catalyst, 1.62 mmol of (dme)NiBr$_2$ and 0.81 mmol LiNP$^t$Cy$_3$ are separately suspended in 5 mL portions of tetrahydrofuran (THF) in 15 mL screw-capped vials under an inert atmosphere, for example, in a nitrogen- or argon-filled drybox. Both suspensions are cooled to −35° C. in a dry-box freezer for an hour. The LiNP$^t$Cy$_3$ suspension is added dropwise into the metal halide suspension with occasional stirring over a four-hour period with the temperature constant at −35° C. After the addition of the ligand, the reaction mixture is left in the freezer overnight. The solvent is removed in vacuo and the residue is washed with 4 mL portions of hexane thrice. The residue is dissolved in 7 mL THF, charged with 2.5 mmol of Na delivered using a 1% Na/Hg reagent and stirred overnight. The solvent is evaporated and the product is extracted with pentane and filtered through a plug of Celite. The solvent is removed. This reaction gave a 50% yield.

Example 3

[Co(NP$^t$Bu$_3$)]$_4$ and Method of Synthesis

A cobalt phosphoranimide catalyst (shown in FIG. 2 and referred to herein as the Co(I) catalyst) having the formula shown below is synthesized as an example:

To prepare this catalyst, 1.62 mmol of CoCl$_2$ and 0.81 mmol LiNP$^t$Bu$_3$ are separately suspended in 5 mL portions of tetrahydrofuran (THF) in 15 mL screw-capped vials under an inert atmosphere, for example, in a nitrogen- or argon-filled drybox. Both suspensions are cooled to −35° C. in a dry-box freezer for an hour. The LiNP$^t$Bu$_3$ suspension is added dropwise into the metal halide suspension with occasional stirring over a four-hour period with the temperature constant at −35° C. After the addition of the ligand, the reaction mixture is left in the freezer overnight. The solvent is removed in vacuo and the residue is washed with 4 mL portions of hexane thrice. The residue is dissolved in 7 mL THF, charged with 2.5 mmol of Na delivered using a 1% Na/Hg reagent and stirred overnight. The solvent is evaporated and the product is extracted with pentane and filtered through a plug of Celite. The solvent is removed. This reaction gave a 65% yield. The product precipitates as prismatic dark brown crystals upon cooling to −35° C. The product is characterized by X-ray crystallography, magnetic susceptibility measurement by the Evan's method.

Figure 2:
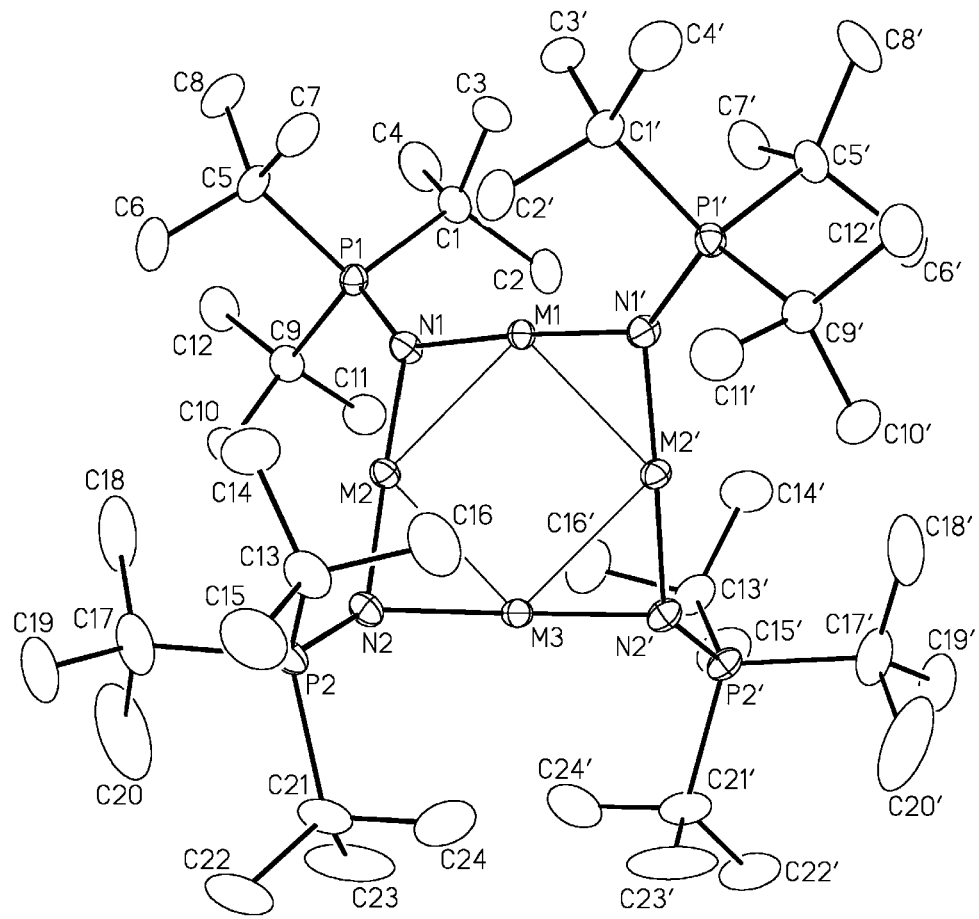
FIG. 2 shows an ORTEP diagram depicting the X-ray crystal structure of $[Co(NP^tBu_3)]_4$.

FIG. 2 shows an ORTEP diagram depicting the X-ray crystal structure of [Co(NP$^t$Bu$_3$)]$_4$. The calculated elemental composition is C, 52.36%; H, 9.89%; N, 5.09%. The determined elemental composition is C, 52.68%; H, 10.09%; N, 4.86%. The solution magnetic susceptibility experiments revealed that the Co(I) catalyst is an 8-electron paramagnet ($\mu_{eff}$=8.98$\mu_{Bo}$) at room temperature.

Example 4

Synthesis of [Cl$_2$Co$_2$(μ-NP$^t$Bu$_3$)$_2$(THF)$_2$]

The stepwise synthesis of the cobalt catalyst is also demonstrated via the isolation and characterization of a halide-functionalized cobalt phosphoranimide complex, [Cl$_2$Co$_2$(μ-NP$^t$Bu$_3$)$_2$(THF)$_2$] (FIG. 3), formed from the anionic ligand metathesis between CoCl$_2$ and LiNP$^t$Bu$_3$. Subsequent reduction of this complex results in the formation of the Co(I) catalyst, [CoNP$^t$Bu$_3$]$_4$. In the halide-functionalized cobalt phosphoranimide complex, the metal centers each bind one THF (solvent) molecule, and has the formula:

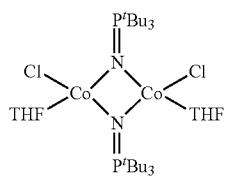

Figure 3:
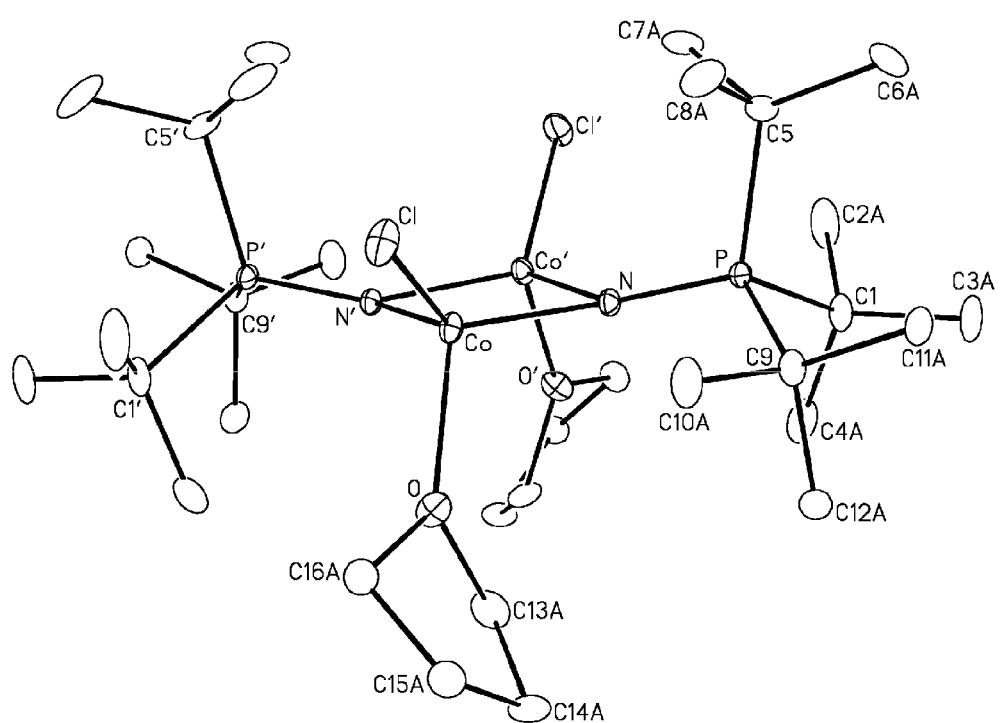
FIG. 3 shows an ORTEP diagram depicting the X-ray crystal structure of $[Co(\mu-NP^tBu_3)Cl(THF)]_2$.

To prepare this catalyst, 1.62 mmol of CoCl$_2$ and 0.81 mmol LiNP$^t$Bu$_3$ are separately suspended in 5 mL portions of tetrahydrofuran (THF) in 15 mL screw-capped vials under an inert atmosphere, for example, in a nitrogen- or argon-filled drybox. Both suspensions are cooled to −35° C. in a dry-box freezer for an hour. The LiNP$^t$Bu$_3$ suspension is added dropwise into the metal halide suspension with occasional stirring over a four-hour period with the temperature constant at −35° C. After the addition of the ligand, the reaction mixture is left in the freezer overnight. The solvent is removed in vacuo and the residue is washed with 4 mL portions of hexane thrice. This reaction gives an 85% yield. X-ray quality crystals can be grown from a concentrated THF solution for recrystallization at −35° C. FIG. 3 shows the ORTEP diagram depicting the X-ray crystal structure of the product.

FIG. 3 shows an ORTEP (Oak Ridge Thermal Ellipsoid Plot Program) diagram depicting the X-ray crystal structure of $[Cl_2Co_2(\mu\text{-}NP^tBu_3)_2(THF)_2]$.

Example 5

Synthesis of $[Co(NP^tBu_3)]_4$ from $[Cl_2Co_2(\mu\text{-}NP^tBu_3)_2(THF)_2]$

All manipulations in this synthesis was carried out under inert atmosphere, for example, in a nitrogen- or argon-filled drybox. 0.5 mmol of $[Cl_2Co_2(L\text{-}NPt\text{---}Bu_3)_2(THF)_2]$ is dissolved in 5 mL THF and then treated with 1.1 mmol Na(Hg) reagent at −35° C. to room temperature 12 hours. The solvent is evaporated and the product is extracted with pentane and filtered through a plug of Celite. The solvent is removed and a concentrated THF solution of the product is prepared for recrystallization. The product precipitates as prismatic dark blue crystals upon cooling to −35° C. The product was identical in all respects to the material obtained above.

Example 6

$[Fe(NP^tBu_3)]_n$ and Method of Synthesis

An iron phosphoranimide catalyst having the formula $[Fe(NP^tBu_3)]_n$ was synthesized.

To prepare this catalyst, 1.62 mmol of $(dme)FeBr_2$ and 0.81 mmol $LiNP^tBu_3$ are separately suspended in 5 mL portions of tetrahydrofuran (THF) in 15 mL screw-capped vials under an inert atmosphere, for example, in a nitrogen- or argon-filled drybox. Both suspensions are cooled to −35° C. in a dry-box freezer for an hour. The $LiNP^tBu_3$ suspension is added dropwise into the metal halide suspension with occasional stirring over a four-hour period with the temperature constant at −35° C. After the addition of the ligand, the reaction mixture is left in the freezer overnight. The solvent is removed in vacuo and the residue is washed with 4 mL portions of hexane thrice. The residue is dissolved in 7 mL THF, charged with 2.5 mmol of Na delivered using a 1% Na/Hg reagent and stirred overnight. The solvent is evaporated and the product is extracted with pentane and filtered through a plug of Celite. The solvent is removed. This reaction forms amorphous dark brown solids at 50% yield.

Example 7

Catalytic Hydrodesulfurization and Hydrogenation

Experiments were carried out to establish the ability of a catalyst of formula $[Co(NP^tBu_3)]_4$ to mediate the catalytic hydrogenation of alkenes, as well as hydrodesulfurization of dibenzothiophene.

An example hydrogenation and a hydrodesulfurization reaction is represented below:

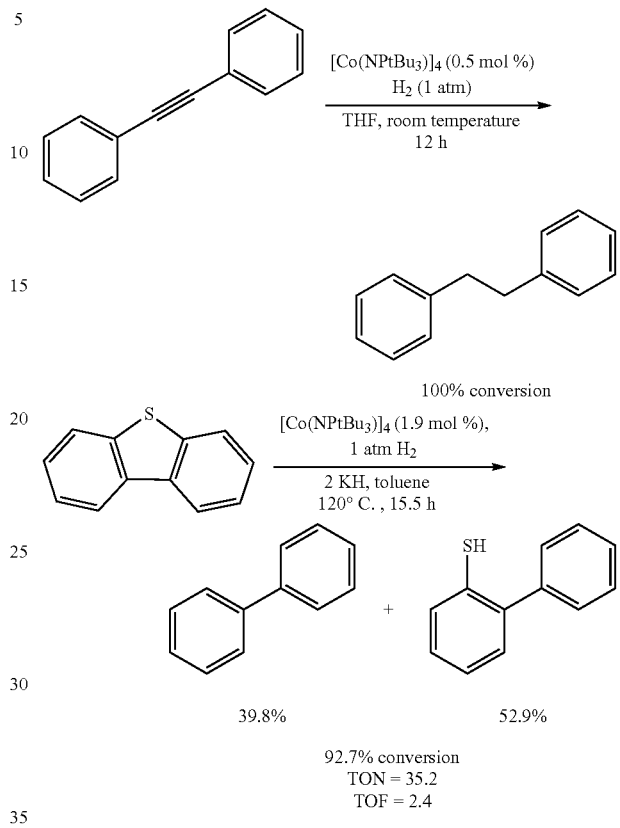

Turnover number ("TON")=moles of substrate (two C—S bonds cleaved) converted per mole of cluster; in cases wherein a mixture of the partially and fully desulfurized products (thiol and hydrocarbon, respectively) was obtained, one catalytic turnover was calculated as two moles of C—S bonds activated per mole of cluster. These numbers were calculated from data obtained from GC-MS analyses.

Turnover frequency ("TOF")=moles of substrate (two C—S bonds cleaved) converted per mole of cluster per hour; in cases wherein a mixture of the partially and fully-desulfurized products (thiol and hydrocarbon, respectively) was obtained, one catalytic turnover was calculated as two moles of C—S bonds activated per mole of cluster per hour.

The invention claimed is:
1. A transition metal catalyst comprising monomeric units of the general Formula I:

[MNPR$_3$]   Formula I where M is a first row transition metal having a +1 oxidation state;
R$_3$PN$^-$ is a monoanioinic phosphoranimide ligand of structure:

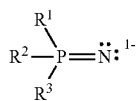

where:
R¹, R², R³ can be the same group or different groups;
R¹, R², R³=alkyl (C1-18, primary, secondary and tertiary alkyl), cycloalkyl (C3-C8), aryl/heteroaryl, substituted aryl/heteroaryl or an inert functional group containing at least one heteroatom selected from the group consisting of a Group 15 and/or Group 16 element;
R¹, R², R³ may also be linked to give cyclic systems, using linkages such as aliphatic cyclic systems;
wherein the M to R³PN⁻ ratio in the catalyst is 1:1.

2. The catalyst of claim 1 of Formula I, wherein the compound of Formula I can form clusters having general Formula II:

   Formula II where:
n is a whole number of at least 2.

3. The catalyst of claim 2, where n=4.

4. The catalyst of claim 1, wherein the transition metal is Fe, Co or Ni.

5. The catalyst of claim 1, wherein R¹, R², R³ are alkyl groups independently selected from the group consisting of methyl, ethyl, n-propyl, isopropyl, sec-butyl and t-butyl.

6. The catalyst of claim 5, wherein R¹, R², R³ are t-butyl.

7. The catalyst of claim 1, wherein R¹, R², R³ are cycloalkyl groups independently selected from the group consisting of cyclopentyl, cyclohexyl, alkyl-substituted cyclopentyl and alkyl-substituted cyclohexyl.

8. The catalyst of claim 7, wherein R¹, R², R³ are cyclohexyl.

9. The catalyst of claim 1, wherein R¹, R², R³ are aryl groups independently selected from the group consisting of phenyl, tolyl, xylyl, naphthanyl and biphenyl.

10. The catalyst of claim 2, having the formula [FeNPR₃]ₙ wherein R can be ethyl, isopropyl, t-butyl or cyclohexyl.

11. The catalyst of claim 2, having the formula [CoNPR₃]ₙ wherein R can be ethyl, isopropyl, t-butyl or cyclohexyl.

12. The catalyst of claim 2, having the formula [NiNPR₃]ₙ wherein R can be ethyl, isopropyl, t-butyl or cyclohexyl.

13. The catalyst of claim 1, having the formula [FeNPᵗBu₃]₄, [CoNPᵗBu₃]₄ or [NiNPᵗBu₃]₄.

14. A method of synthesis of a transition metal catalyst comprising:
reducing a complex of Formula IV [MNPR₃X₍ₘ₋₁₎]ₙ with a reducing agent to produce a catalyst of Formula I [MNPR3], wherein Formula IV is

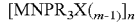

where:
m=2 to 3;
n=1 to 4;
M is Fe, Co or Ni;
X⁻ can be any halide or pseudohalide;
R₃PN⁻ is a monoanioinic phosphoranimide ligand of structure:

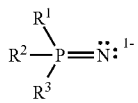

where
R¹, R², R³ are the same group or different groups;
R¹, R², R³=alkyl (C1-18, primary, secondary and tertiary alkyl), cycloalkyl (C3-C8), aryl/heteroaryl, substituted aryl/heteroaryl or an inert functional group optionally containing at least one heteroatom, and wherein the substituents may also be linked to give cyclic systems, both aliphatic and aromatic;
the M:NPR3 ratio is 1:1;
and wherein in Formula I, M and NPR₃ are as defined for the compound of Formula II and wherein the M:NPR3 ratio is 1:1.

15. The method of claim 14, wherein the reducing agent is selected from the group consisting of Li, Na, K, sodium naphthalenide, Na(Hg) amalgam, Na—K alloy, and KC₈.

16. The method of claim 14, wherein the ratio of the reducing agent to complex of Formula II ranges from 1:1 to 5:1.

17. The method of claim 14, wherein the reduction step can be conducted at temperatures ranging from about −80 to 40° C., when the reaction is carried out in an inert organic solvent.

18. The method of claim 14, wherein the temperature ranges from −80 to 30° C.

19. The method of synthesis of claim 14, wherein the reduction step can be carried out in an inert organic solvent selected from the group consisting of tetrahydrofuran, hexane, benzene, diethyl ether and toluene.

20. A method of synthesis of complex of Formula IV from an anionic metathesis reaction between a metal salt selected from the group consisting of MXₘ and LₐMXₘ and an alkali or alkaline metal salt of a phosphoranimide ligand, wherein Formula IV is defined as follows:

where:
m=2 to 3;
n=1 to 4;
M is Co or Ni,
X⁻ can be any halide or pseudohalide;
R₃PN⁻ is a monoanioinic phosphoranimide ligand of structure:

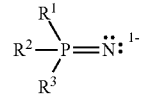

Where:
R¹, R², R³ can be the same group or different groups;
R¹, R², R³=alkyl (C1-18, primary, secondary and tertiary alkyl), cycloalkyl (C3-C8), aryl/heteroaryl, substituted aryl/heteroaryl or an inert functional group optionally containing at least one heteroatom, and wherein the substituents may also be linked to give cyclic systems, both aliphatic and aromatic;
the ratio of NPR3 to M is 1:1; and
wherein in MXₘ and LₐMXₘ:
m=2 to 3;
a=1 to 4;
M can be any first row transition metals;
X⁻ can be any halide or pseudohalide;
L is a two-electron dative donor molecule selected from the group of dialkyl ethers consisting of tetrahydrofuran, 1,2-dimethoxyethane, dioxane; or selected from the group consisting of trialkylphosphine or a triarylphosphine selected from the group consisting of triphenylphosphine and tri-(p-tolyl)phosphine.

21. The method of claim 20, wherein metal phosphoranimide salts of formula M'(NPR₃)ᵦ or [Mg(NPR₃)X] are used for the anionic metathesis
where:
b=1 or 2;
X⁻ can be any halide;
M' can be an alkali or alkaline metal; and
NPR3 is defined as in the compound of Formula II.

22. The method of claim 20, wherein the ratio of the metal salt to $M'(NPR_3)_b$ ranges from 1:1 to 5:1.

23. A method of synthesis of complex of Formula IV from an anionic metathesis reaction between a metal salt selected from the group consisting of $MX_m$ and $L_aMX_m$ and an alkali or alkaline metal salt of a phosphoranimide ligand, wherein Formula IV is defined as follows:

$$[MNPR_3X_{(m-1)}]_n$$

where:

m=2 to 3;

n=1 to 4;

M is Fe, Co or Ni, $X^-$ can be any halide or pseudohalide;

$R_3PN^-$ is a monoanioinic phosphoranimide ligand of structure:

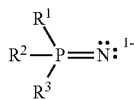

Where:

$R^1, R^2, R^3$ can be the same group or different groups;

$R^1, R^2, R^3$=alkyl (C1-18, primary, secondary and tertiary alkyl), cycloalkyl (C3-C8), aryl/heteroaryl, substituted aryl/heteroaryl or an inert functional group optionally containing at least one heteroatom, and wherein the substituents may also be linked to give cyclic systems, both aliphatic and aromatic;

the ratio of NPR3 to M ranges from 2:1 to 4:1 wherein in $MX_m$ and $L_aMX_m$;

m=2 to 3;

a=1 to 4;

M can be any first row transition metals;

$X^-$ can be any halide or pseudohalide; and,

L can be a two-electron dative donor molecule selected from the group of dialkyl ethers consisting of tetrahydrofuran, 1,2-dimethoxyethane, dioxane; or selected from the group consisting of trialkylphosphine or a triarylphosphine selected from the group consisting of triphenylphosphine and tri-(p-tolyl)phosphine.

* * * * *